United States Patent [19]

McCarthy

[11] 4,440,861
[45] Apr. 3, 1984

[54] SOLAR APPARATUS AND PROCESS

[75] Inventor: Walton W. McCarthy, Bozeman, Mont.

[73] Assignee: Entropy Dynamics, Bozeman, Mont.

[21] Appl. No.: 307,610

[22] Filed: Oct. 1, 1981

Related U.S. Application Data

[63] Continuation-in-part of Ser. No. 187,348, Sep. 15, 1980, Pat. No. 4,345,974.

[51] Int. Cl.³ .................. B01D 3/00; C07C 29/80; C12C 7/08; C12M 1/02
[52] U.S. Cl. .................... 435/306; 435/161; 435/316; 34/93; 126/417; 126/437; 126/450; 159/15; 202/185 D; 202/197; 202/234; 203/19; 203/DIG. 1; 203/DIG. 13; 366/64; 366/167
[58] Field of Search ............... 203/18, 19, 100, 87, 203/DIG. 1, 39, DIG. 13, DIG. 16; 202/185 D, 205, 234, 197, 179, 198, 176; 435/161, 162, 303, 306, 316, 813; 159/1 S; 34/93; 126/417, 437, 450; 366/64, 165, 167, 184, 279

[56] References Cited

U.S. PATENT DOCUMENTS

| | | | |
|---|---|---|---|
| 102,633 | 5/1870 | Wheeler et al. | 203/DIG. 1 |
| 245,998 | 8/1881 | Davies | 435/306 |
| 4,249,317 | 2/1981 | Murdock | 203/DIG. 1 |
| 4,286,066 | 8/1981 | Butler | 203/DIG. 1 |
| 4,304,176 | 12/1981 | Redl | 435/306 |
| 4,306,940 | 12/1981 | Zenty | 203/DIG. 1 |
| 4,309,254 | 1/1982 | Dahlstrom et al. | 203/DIG. 13 |
| 4,314,890 | 2/1982 | Beck et al. | 203/19 |
| 4,345,974 | 8/1982 | McCarthy | 203/19 |
| 4,371,623 | 2/1983 | Taylor | 203/19 |

Primary Examiner—Wilbur L. Bascomb, Jr.
Attorney, Agent, or Firm—Arthur L. Urban

[57] ABSTRACT

Solar apparatus for producing alcohol including a frame portion, a heating portion, a slurry-forming portion, a fermentation portion, a distillation portion, a condensation portion and a drying portion; the heating portion including a plurality of solar panel members, the slurry-forming portion including a hammer mill and a frusto-conical section thereunder, the frustoconical section including a tangential liquid inlet opening and a tangential slurry outlet opening, the fermentation portion including a fermentation chamber, a pump disposed adjacent the chamber, inlet and outlet conduits extending between the pump and the bottom of the chamber, the distillation portion including a base section and a face section, the face section including a conduit having a circuitous path, the condensation portion including a first chamber, a second chamber extending downwardly within the first chamber partway down from the top, a spiral conduit disposed within the first chamber, the drying portion including a solar air heating section, a solids storage, a rotatable cylindrical member horizontally disposed, a liquid collector and a liquid storage. Also, solar heating apparatus, slurry-forming apparatus, fermentation apparatus, solar distillation apparatus, condensation apparatus, solar drying apparatus and a solar process.

1 Claim, 9 Drawing Figures

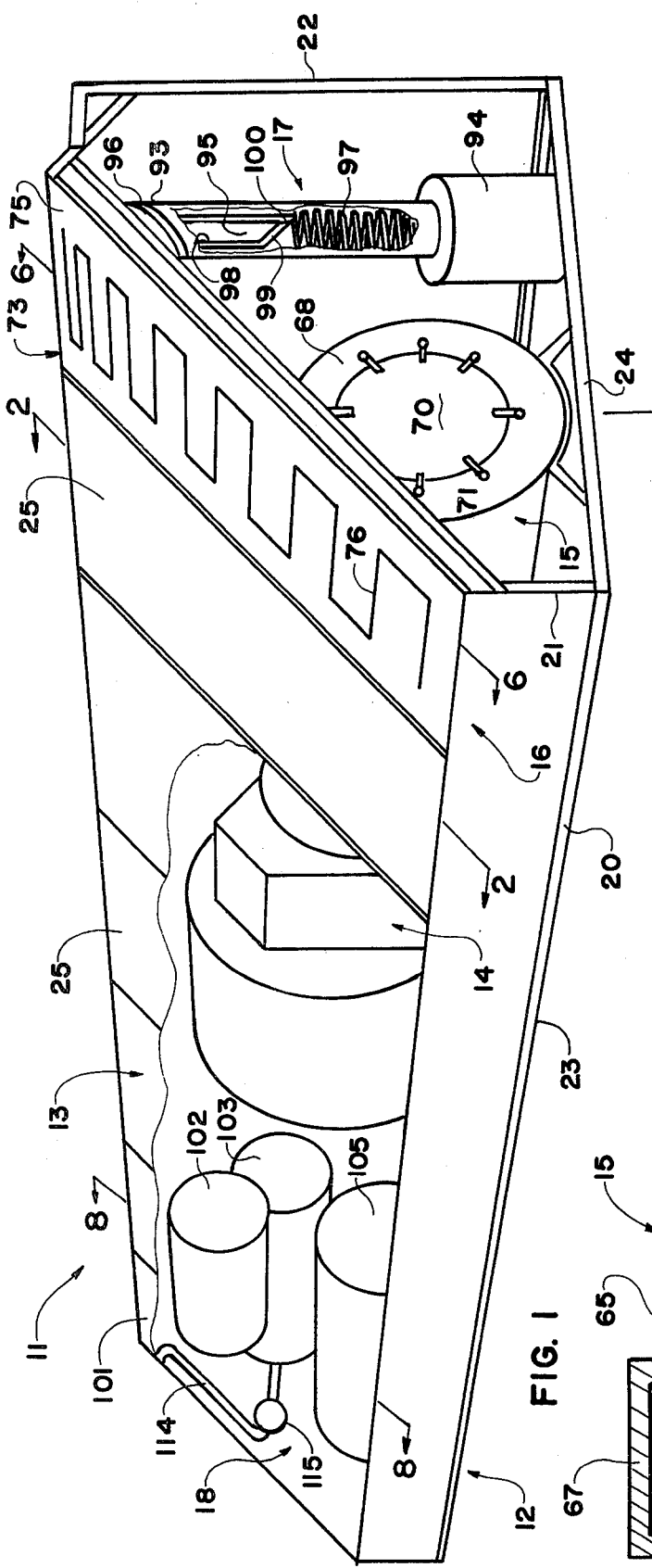
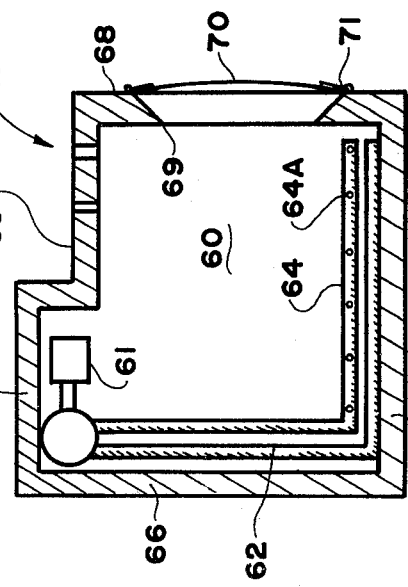
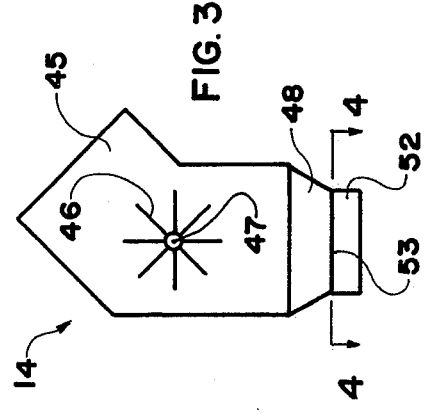
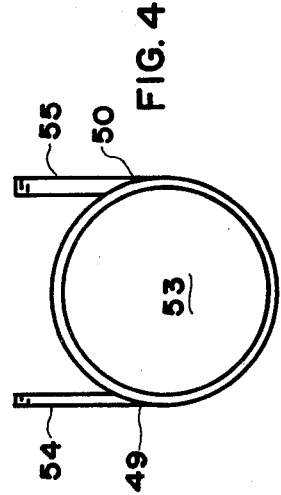

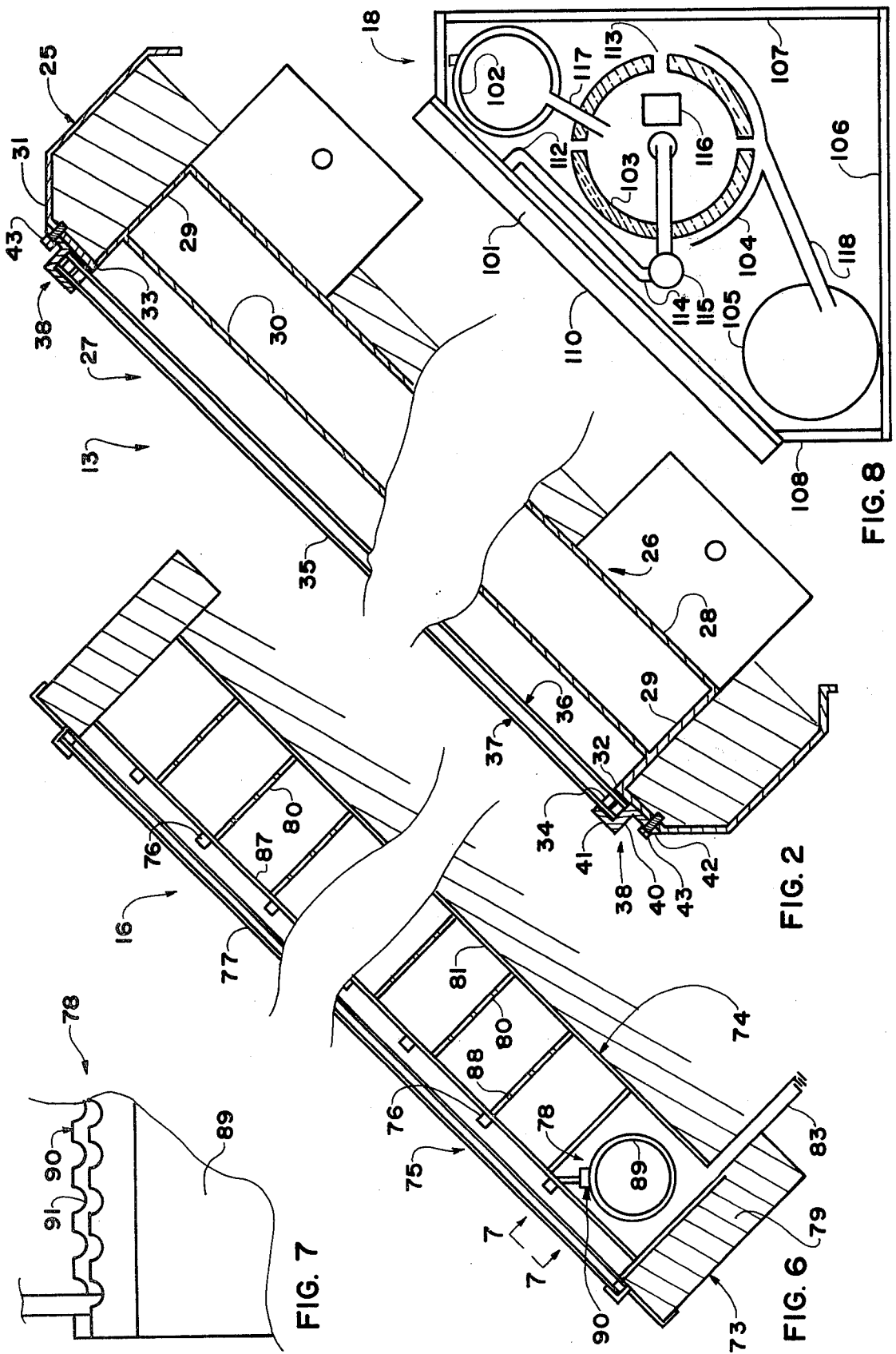

SOLAR APPARATUS AND PROCESS

This application is a continuation-in-part of pending application Ser. No. 187,348, filed Sept. 15, 1980, now U.S. Pat. No. 4,345,974.

This invention relates to a novel solar apparatus and process and more particularly relates to a new solar apparatus and process for producing alcohol.

Alcohol and similar products have been produced by a variety of methods through the years. Ordinarily, alcohol is produced by fermenting an organic material such as grain or another plant derivative. This may be accomplished, for example, by allowing the organic material to decay or ferment naturally or by the application of heat. After fermentation, the solid material is separated from the liquid which is primarily a mixture of water and alcohol. The alcohol is separated from the mixture by distillation. The mixture is heated until one of the components is vaporized or boiled from the mixture. The vapors are condensed on a cool surface and the condensed liquid collected.

Heating of the fermentable material generally is done by using conventional fossil fuels such as oil, natural gas, coal and the like. With the large increases in the cost of such fuels in recent years, the cost of alcohol has increased drastically. The price increases of most alcoholic products such as alcoholic beverages, medicines and the like have been accepted by the public because their costs do not represent a significant proportion of a family's budget.

However, the recent increases in the cost of fossil fuels has greatly increased interest in alcohol as a fuel source. One of the principal areas of interest is the blending of alcohol with gasoline to form a product called "gasohol". Gasohol which usually comprises about 10% alcohol and 90% gasoline can be used in place of straight gasoline in internal combustion engines without changing the engine.

One of the problems with gasohol is its high cost. Although alcohol is more costly to produce than gasoline, interest in gasohol continues because it provides a way of reducing the dependency of the United States on imported oil. Thus, the U.S. government currently is subsidizing the production of alcohol for gasohol. In spite of the subsidy, there is a general uneasiness about increasing the use of gasohol because of concern that the subsidy may be withdrawn. Thus, there has been limited investment in commercial alcohol plants for gasohol.

In view of the large supplies of fermentable materials such as grains in the United States and the ever increasing cost of imported petroleum, there continues to be considerable effort directed to finding less expensive ways to produce alcohol. In spite of these efforts, there still remain major deterrents to the success, that is, the cost of the raw material and the energy requirements for producing alcohol.

The present invention provides a novel apparatus and process for producing alcohol. The apparatus and process of the invention produce alcohol at less cost than previously known procedures. The apparatus and process utilize solar energy in a unique way to produce alcohol.

The apparatus and process of the present invention are relatively simple to use. The apparatus can be installed by an ordinary homeowner or farmer with a minimum of instruction. The process of the invention can be carried out by a layman without special knowledge or skills.

The apparatus of the invention is simple in design and can be fabricated from commercially available components and materials. The apparatus can be manufactured relatively inexpensively. The apparatus can be transported conveniently on a flat bed truck and requires a minimum of installation on the site. The apparatus has a long useful life and requires little maintenance.

Other benefits and advantages of the novel solar apparatus and process of the present invention will be apparent from the following description and the accompanying drawings in which:

FIG. 1 is a view in perspective of one form of the solar apparatus of the invention for producing alcohol;

FIG. 2 is an enlarged fragmentary sectional view of the heating portion of the solar apparatus taken along line 2—2 of FIG. 1;

FIG. 3 is a side view of the slurry-forming portion of the solar apparatus shown in FIG. 1;

FIG. 4 is an enlarged sectional view of the slurry-forming apparatus taken along line 4—4 of FIG. 3;

FIG. 5 is a sectional view of the fermentation portion of the solar apparatus taken along line 5—5 of FIG. 1;

FIG. 6 is an enlarged fragmentary sectional view of the distillation of the solar apparatus taken along line 6—6 of FIG. 1;

FIG. 7 is a further enlarged fragmentary view of the distribution part of the distillation portion taken along line 7—7 of FIG. 6;

FIG. 8 is a sectional view of the drying portion of the solar apparatus taken along line 8—8 of FIG. 1.

Figure 9:
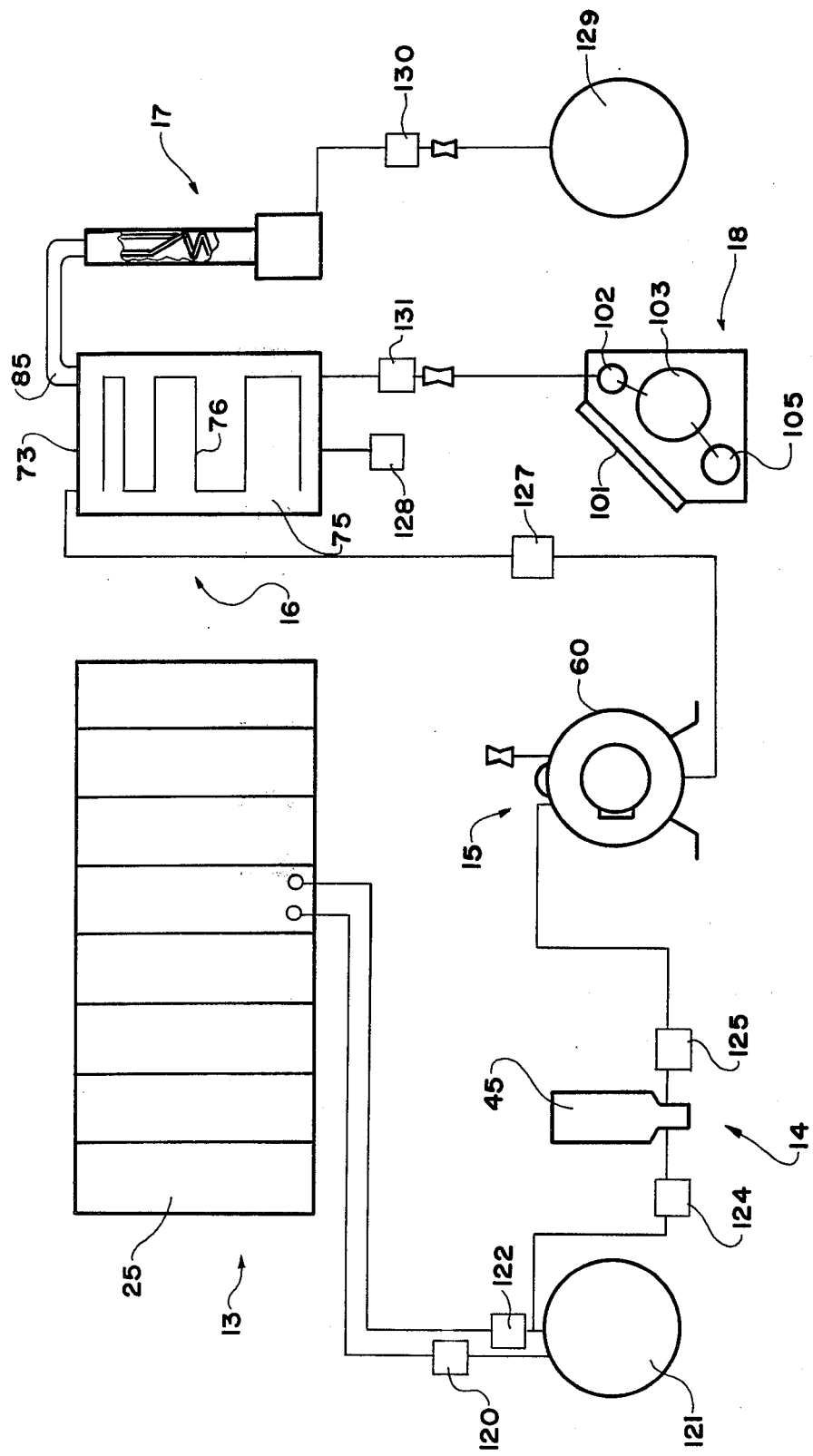
FIG. 9 is a schematic illustration of one form of the solar process of the invention for producing alcohol.

As shown in the drawings, one form of the novel solar apparatus 11 of the invention for producing alcohol includes a frame portion 12, a heating portion 13, a slurry-forming portion 14, a fermentation portion 15, a distillation portion 16, a condensation portion 17 and a drying portion 18.

The frame portion 12 of the solar apparatus includes a base section 20 having a length substantially greater than the width thereof. Upstanding sections 21 and 22 extend upwardly from each longitudinal edge 23 of the base section 20. One of the upstanding sections shown as section 22 has a height substantially greater than the other upstanding section 21. The base section 20 and the longitudinal sections 21 and 22 as well as cross members 24 may be formed of suitable structural members such as steel girders and the like.

The heating portion 13 includes a plurality of solar panel members 25. The panel members 25 are arranged side by side along the length of the apparatus 11 with each panel member extending between the upstanding sections 21 and 22 of the frame portion 12.

The solar heating panels 25 each include a pan portion 26 and cover portion 27. The pan portion 26 has a generally rectangular configuration including a bottom section 28 and sidewall sections 29. An intermediate section 30 extends between the sidewall sections 29 below the peripheral edges 31 thereof. The sidewall sections 29 include flat top sections 32 and 33 that are oriented in the same plane and substantially parallel to the bottom section 28.

The cover portion 27 of the panels 25 includes a plurality of spaced transparent layers 35. The layers 35 extend between the top sections 32 and 33 of the sidewall sections 29. Pairs of the transparent layers 35 are combined with a window assembly 35. In the window assembly 36, and layers are spaced from one another and a partial vacuum is effected in the space between the layers. Suitable window assemblies are commercially available as insulating glass windows.

One of the window assemblies 36 has its periphery in contact with the top sections 32 and 33 of the sidewall sections 29. A second window assembly 37 is disposed over and spaced from the first window assembly 36. Peripheral spacer means 34 is positioned between the first and second window assemblies.

A peripheral flange member 38 with a generally reverse double right angle cross-sectional configuration secures the window assemblies 36 and 37 to the pan section 26. The connecting section 40 of the flange member 38 bears against the edges of the first and second window assemblies 36 and 37. One flange section 41 bears against the top of the second window assembly 37. The other flange section 42 bears against the exposed portion of the top sections 32 and 33. Fastening means such as bolts 43 secure the flange member 38 to the top sections.

The slurry-forming portion 14 of the apparatus 11 is disposed below the heating portion 13. The slurry-forming portion 14 includes hammer mill means 45 with a plurality of hammer arms 46 pivotally connected to a rotatable shaft 47. Under the hammer mill 45 is disposed a frustoconical section 48. The frustoconical section 48 as shown in FIG. 4 includes a tangential liquid inlet opening 49 and a tangential slurry outlet opening 50.

Advantageously, the frustoconical section 48 has its smaller diameter adjacent and affixed to a free edge of an upstanding support section 52. The frustoconical section 48 includes a closed bottom section 53. Liquid inlet opening 49 and slurry outlet opening 50 are disposed adjacent the periphery of the bottom section 53. The inlet and outlet openings communicate with substantially parallel inlet and outlet conduits 54 and 55, respectively. The inlet and outlet conduits 54 and 55 extend from the same side of the periphery of bottom section 53 as shown.

Preferably, the inlet opening 49 has a diameter significantly smaller than the diameter of the outlet opening 55. Also, the frustoconical section 48 has an upper diameter approximately twice the lower diameter and a height substantially equal to the lower diameter.

The fermentation portion 15 also is disposed below the heating portion 13. The fermentation portion 15 includes a fermentation chamber 60 and pump means 61 disposed adjacent the chamber. An inlet conduit 62 extends between the pump 61 and the bottom 63 of the chamber 60. An outlet conduit 64 extends downwardly from the pump 61 and adjacent the bottom of the chamber. The section of the outlet conduit disposed adjacent the bottom 63 includes a plurality of discharge openings 64A.

The fermentation portion 15 advantageously includes a cylindrical body 65 with an end section 66 covering one end of the body. A pump housing 67 extends outwardly from the top of the body. The housing has a cross-sectional size significantly smaller than that of the cylindrical body 65 with a length significantly less than that of the body. The housing 67 communicates with the interior of the body. An access section 68 covers the opposite end of the body 65 and includes a hatch opening 69 and a hatch cover 70. Means such as flanges 71 around the periphery of the hatch opening 69 secure the hatch cover.

The distillation portion 16 includes a solar panel member 73 extending between the upstanding sections 21 and 22 of the frame portion 12. The panel member 73 includes a base section 74 and a face section 75. The face section 75 includes a conduit 76 having a circuitous path. Transparent layers 77 extend over the face section 75. Distributing means 78 is disposed under the lower end 79 of the face section. A plurality of spaced baffles 80 extend from the face section 75 to the base section 74.

Advantageously, the distillation portion 16 includes a generally rectangular inclined pan section 81, which preferably has insulated bottom and sidewalls. A plurality of spaced transparent layers 77 extend between the peripheral edges of the pan section 81 and enclose the cavity therein. The pan section 81 includes an outlet 83 adjacent a lower end thereof. A vapor outlet opening 85 is located adjacent an upper end of the pan section.

As shown, the face section 75 of the distillation portion 16 preferably includes a substantially flat plate plate member 87 which is disposed within the cavity of the pan section 81 closely adjacent to the transparent layers 77. The conduit 76 extends from one end of plate member 87 to the other, advantageously in a zigzag path. The baffles 80 are disposed transversely of the pan section 81 and are arranged substantially parallel to one another. Each of the baffles includes a plurality of spaced openings 88 therethrough.

A tubular member 89 is disposed adjacent the lower end of the pan section 81 of the distillation portion 16. The tubular member 89 is disposed between and substantially parallel to the lower end of the pan section 81 and the baffles 80 closest thereto. The tubular member 89 includes an open channel member 90 extending upwardly from the top thereof with the free edges of the channel section including a plurality of recesses 91 along the length thereof.

The condensation portion 17 may be disposed below the distillation portion 16. The condensation portion 17 includes a first chamber shown as section 93 that extends upwardly advantageously from a liquid collector section 94. A second chamber shown as smaller section 95 extends downwardly within the first section 93. The second section 95 extends partway down from the top of the first section 93 which preferably includes a cover section 96. A spiral conduit 97 is disposed within the lower part of the first section 93. The conduit 97 communicates with the lower end of the second section 95.

The second section 95 advantageously includes an inlet opening 98 communicating with the upper portion thereof. Also, the second section 95 may include a tapered bottom section 99 with an outlet opening 100 disposed at the lowest part of the bottom. The conduit 97 has one end connected to the outlet opening 100 of the second section 95. The lower end of the conduit 97 is connected to an inlet of the collector section 94.

The drying portion 18 of the solar apparatus 11 of the invention includes a solar air heating section 101 shown as a panel similar to panel members 25. The drying portion 18 is disposed adjacent to the heating portion 13. The drying portion includes a wet solids storage means such as tank 102 and a rotatable cylindrical member 103 horizontally disposed below the tank. Liquid collecting means 104 is disposed below the cylindrical member 103 and closely adjacent thereto. Liquid storage means 105 is associated with the collecting means 104.

The drying portion 18 preferably includes a base section 106 and sidewall sections 107 and 108 extending upwardly from the base section. One of the upstanding sections 107 is substantially higher than the other upstanding section 108. The solar heating panel 101 extends between the sidewall sections 107 and 108. The solar panel 101 includes a plurality of transparent layers 110 thereover. Outlet openings 112 communicates with the interior of the panel member 101.

The cylindrical member 103 has a number of widely spaced openings 113 in the periphery thereof which advantageously is insulated. Conduit 114 connects the outlet opening 112 of the panel member 101 with the interior of the cylindrical member 103. A fan 115 is disposed along the length of the conduit 114. Means such as motor 116 are provided for rotating the cylindrical member 103.

The wet solids storage means 102 advantageously is located above the cylindrical member 103 and the liquid storage means 105 below the cylinder 103. Conduits 117 and 118 connect the cylindrical member 103 with the storage means 102 and 105.

The solar process for producing alcohol in accordance with the present invention as illustrated particularly in FIG. 9 includes the steps of monitoring independently the temperature of the water in storage chamber 121 and in the solar heating panels 25 through control 120. Water is transferred back and forth between panels 25 and chamber 121 to the respective area having the higher temperature through the use of pump 122. In this way the water is pumped into the panels 25 and exposed to solar radiation when the temperature therein is above that of chamber 121. When the temperature of the water in panels 25 is below that of chamber 121, such as at night, the water in the panels is pumped back to the storage chamber until the temperature differential changes. This sequence continues until the temperature of the water in chamber 121 ordinarily reaches between about 190°-200° F.

Fermentable material is reduced to a finely divided state in hammer mill 45. The fermentable material may be any of a wide variety of plant materials such as grains, vegetables, silage and especially sugar beets, potatoes, comfrey and the like. Although some of the materials may require little if any reduction in size, they may need to be crushed to break a hard shell or covering.

The heated water from chamber 121 is transferred by pump 124 to mixer 48 where it is combined with the fermentable material from mill 45 to form a slurry. The slurry is transferred with pump 125 to fermentation chamber 60. The slurry is maintained in the chamber at a temperature of about 100° F. for a period sufficient to ferment the fermentable material substantially completely. Normally, about 24 to 48 hours achieves substantially complete fermentation using yeast and other enzymes. Periodically during the fermentation step, the slurry is recirculated within the chamber using pump 61.

The fermented slurry is transferred by pump 127 to distillation member 73. The slurry passes through conduit 76 while being exposed to solar radiation to heat the slurry. The heated slurry then is transferred into the chamber behind the face section 75 which is maintained at a subatmospheric pressure with vacuum pump 128.

As the heated slurry is introduced into the subatmospheric chamber, the water and alcohol therein are rapidly evaporated therefrom. The alcohol and water vapor mixture passes upwardly through a tortuous path through the openings 88. The water vapor having a significantly higher boiling point condenses first as the vapor moves toward the top of the chamber.

The alcohol rich vapor moves into the condensation portion 17 where it is cooled and condenses. The alcohol is transferred to storage tank 129 with pump 130. The wet solids from distillation panel 73 are passed to drying portion 18. The solids are transferred to storage tank 102 with pump 131 and then into rotating cylinder 103 where heated air from panel 101 passes through the tumbling solids. The dried material may be used for a number of uses such as animal feed, soil conditioners and the like. The liquid removed from the solids flows through openings 113 in the cylinder 103 and into collector 104 and then transferred to storage tank 105.

The above description and the accompanying drawings show that the present invention provides a novel apparatus and a novel process for producing alcohol at less cost than previous procedures. The process and apparatus produce alcohol through a unique utilization of solar energy.

The apparatus and process of the present invention can be installed easily by a homeowner or farmer after only a minimum of instruction. The apparatus and process are relatively simple to use. The process can be conducted by a layman without special knowledge or skills.

The apparatus of the invention is simple in design and can be manufactured relatively inexpensively. The apparatus can be fabricated from commercially available components and materials using industrial fabricating techniques and semi-skilled labor.

The apparatus can be transported conveniently to the installation site on a flat bed truck. The apparatus of the invention requires a minimum of erection and installation on the site before operation can be started. The apparatus is durable in construction and has a long useful life. The apparatus requires little maintenance.

It will be apparent that various modifications can be made in the particular solar apparatus and process of the invention described in detail and shown in the drawings within the scope of the invention. The size, configuration and arrangement of components can be changed to meet specific requirements. Also, the fermentable material selected can utilize materials that are readily available locally at relatively low cost. In addition, the transfer of materials through the apparatus and process can be effected in other ways. Therefore, the scope of the present invention is to be limited only by the following claims.

What is claimed is:

1. Solar apparatus for producing alcohol including a frame portion, a heating portion, a slurry-forming portion, a fermentation portion, a distillation portion, a condensation portion and a drying portion; said frame portion including a base section having a length substantially greater than the width thereof, upstanding sections extending upwardly from each longitudinal ege of said base section, one of said upstanding sections having a height substantially greater than the other upstanding section; said heating portion including a plurality of solar panel members, said panel members being disposed adjacent to one another, said panel members extending between said upstanding sections of said frame portion; said slurry-forming portion being disposed below said heating portion and including hammer mill means and a frustoconical section thereunder, said frustoconical section including a tangential liquid inlet opening and a tangential slurry outlet opening; said fermentation portion being disposed below said heating portion and including a fermentation chamber, pump means disposed adjacent said chamber, an inlet conduit extending between said pump means and the bottom of said chamber, an outlet conduit extending downwardly from said pump means and adjacent the bottom of said chamber and having a plurality of discharge openings therealong; said distillation portion including a solar panel member extending between said upstanding sections, said solar panel member including a base section and a face section, said face section including a conduit having a circuitous path, transparent layers over said face section, distributing means disposed under the lower end of said face section, a plurality of spaced baffle means extending from said face section to said base section; said condensation portion being disposed below said distillation portion and including a first chamber, a second chamber extending downwardly within said first chamber partway down from the top, a spiral conduit disposed within said first chamber and communicating with the lower end of said second chamber; said drying portion including a solar air heating section disposed adjacent to said heating portion, a solids storage means, a rotatable cylindrical member horizontally disposed below said solar heating section, liquid collecting means disposed below said cylindrical member, and liquid storage means associated with said collecting means.

* * * * *